(12) United States Patent
Asch et al.

(10) Patent No.: US 6,638,219 B1
(45) Date of Patent: Oct. 28, 2003

(54) METHOD OF MAPPING INTERNAL 3-D STRUCTURE OF DENTAL FORMATIONS

(75) Inventors: Herbert A. Asch, Cincinnati, OH (US); Richard E. Klaassen, West Chester, OH (US)

(73) Assignee: Asch-Klaassen Sonics, Inc., Cincinnati, OH (US)

(*) Notice: Subject to any disclaimer, the term of this patent is extended or adjusted under 35 U.S.C. 154(b) by 0 days.

(21) Appl. No.: 10/043,445

(22) Filed: Jan. 10, 2002

Related U.S. Application Data

(60) Provisional application No. 60/261,064, filed on Jan. 11, 2001.

(51) Int. Cl.[7] .......................... A61B 8/00; A61B 5/117; A61C 5/00
(52) U.S. Cl. .................. 600/437; 433/214; 600/587
(58) Field of Search ................................ 600/437, 443, 600/447, 587; 433/214, 72; 73/614

(56) References Cited

U.S. PATENT DOCUMENTS

| 4,043,181 | A | * | 8/1977 | Nigam ........................ 73/614 |
| 4,610,255 | A | * | 9/1986 | Shimura et al. ............. 600/443 |
| 5,006,984 | A | * | 4/1991 | Steele ........................ 600/587 |
| 5,269,309 | A | * | 12/1993 | Fort et al. .................... 600/447 |
| 5,755,571 | A | * | 5/1998 | Companion .................. 433/72 |
| 6,050,821 | A | * | 4/2000 | Klaassen et al. ............ 433/214 |

\* cited by examiner

Primary Examiner—Marvin M. Lateef
Assistant Examiner—Ruby Jain

(57) ABSTRACT

Dental formations, including teeth, gums and supporting bone structure within the oral cavity, can be mapped by ultrasonic scanning technique, thus allowing examination and diagnosis of conditions within the intraosseous environment, including hard and soft tissue. The mapping technique can provide highly resolved details of formations, such as teeth and bridges, and their resident defect, including caries and cracks. The mapped data allow for a more precise and accurate diagnosis for the dental patient, and it provides the dentist with a detailed archive for diagnosis.

9 Claims, 2 Drawing Sheets

METHOD OF MAPPING INTERNAL 3-D STRUCTURE OF DENTAL FORMATIONS

CROSS-REFERENCE TO RELATED APPLICATION

This application claims the benefit of Provisional Application No. 60/261,064, filed Jan. 11, 2001.

BACKGROUND OF THE INVENTION

When diagnosing a dental condition, a dentist can use a series of subjective tools to estimate the nature and severity of the condition. These tools include: a patient's complaint; a visual examination for coloration or structural abnormalities; and, a selective physical probing for relative variations in tooth hardness. Each of these observational tools is non-quantitative, and the results are recorded manually using non-specific terminology.

Dentists also use radiography, which allows for a physical record to be generated which can be read by subsequent diagnosticians, but it does not offer detection of all the possible conditions relevant to dental treatment.

Potential problems arising from use of the above diagnostics might include: inadequate treatment; excessive treatment; lack of acceptable documentation of diagnoses for submission to insurance companies for reimbursement; and, lack of objective documentation of diagnoses for defense to legal claims arising from failed treatments.

The dental establishment continues to endeavor to provide the optimal service to patients in spite of the risks posed by flawed or inadequate diagnoses. Consequently, all parties would benefit from a system of acquiring objective, quantitative, in vivo diagnostic data such as provided by the disclosed method and apparatus.

DESCRIPTION OF THE PRIOR ART

It is well established from laboratory studies that ultrasound can be used to detect a variety of dental conditions, including smooth surface lesions (U.S. Pat. No. 6,162,177), jawbone cavitations (U.S. Pat. No. 6,030,221), and the status of root canal treatment (U.S. Pat. No. 5,115,813). The disclosures in these patents relate to research conducted in the late 1960s and early 70s: For instance, Ultrasonic Pulse-Echo Measurements in Teeth, Arch Oral Biol; 14:745, 1969, Barber et al., and Ultrasonic Measurement of Dental Enamel Demineralization; Ultrasonics, 9:269, 1973, Gerhard et al.

Additionally, an application using an ultrasonic array probe to evaluate oral topography is described in U.S. Pat. No. 6,050,821, which issued Apr. 18, 2000.

SUMMARY OF THE INVENTION

Notwithstanding the methods and techniques previously employed to diagnose dental conditions and to acquire ultrasonic data from dental structures, there is a continuing need for refined and enhanced procedures which can be characterized as follows: A method of mapping the internal structure of dental formations by emitting an ultrasonic pulse to impinge on said structure, and recording the ultrasonic response of said impinged formation, said method comprising:

providing a transducer means positioned to produce an outgoing ultrasonic pulse for impinging directly on said dental formation;

measuring the ultrasonic response from said dental formation; and displaying a representation of said response to depict the internal structure of said dental formation.

The foregoing method can be implemented by an apparatus for mapping the internal structure of a dental formation, said apparatus comprising:

a transducer array for emitting and detecting ultrasonic pulses;

an articulating means to move said transducer array over and around said dental formation;

a power source for activating the movement of said articulating means;

an electrical power source for exciting said transducer array;

an amplification means for enhancing said ultrasonic response; and a computing means for converting said ultrasonic response into an interpretable display.

DESCRIPTION OF THE PREFERRED EMBODIMENTS

Figure 1:
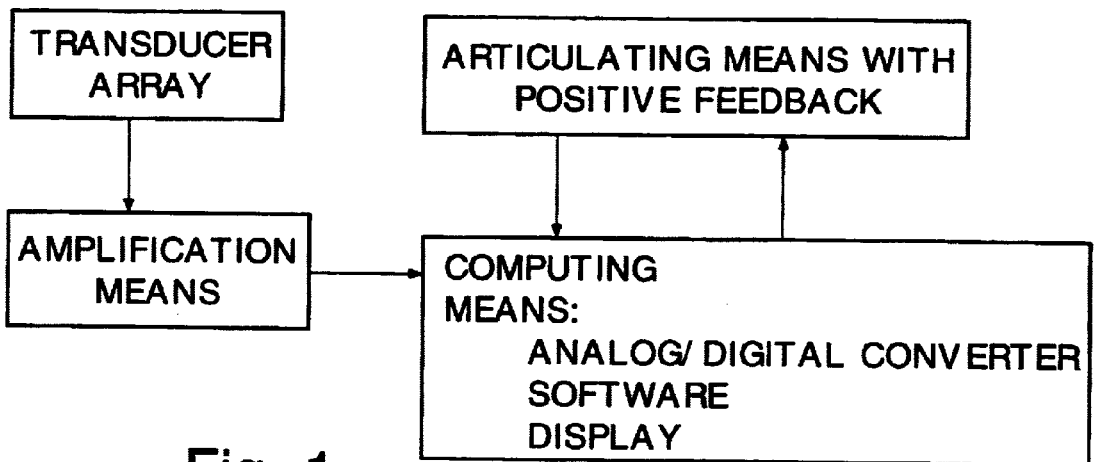
FIG. 1 is a schematic block diagram of the instrumentation of an ultrasonic mapping apparatus.

By using the disclosed ultrasonic data acquisition method, a dental office can add a new means of collecting and archiving patient information. For routine cases, a dental condition can be detected, measured and documented by a series of electronic tools that can be linked to generate a single report. For mildly complex cases, the dentist can compare an ultrasonic data set to archived data to find which known conditions yielded similar ultrasonic responses previously. For the truly unique situation, a dentist can submit the data set to a remote expert for diagnosis, or for comparison to a modeled response. In each case, this can be done electronically, which means that a diagnosis can be made immediately and treatment begun immediately thereafter. The analysis leading to a diagnosis could include any dental formation, including the gums and supporting bone structure. For instance, an analysis could describe features within the tooth itself, such as carries or cracks, or the supporting and surrounding bone or the temperomandibular joint in static and dynamic conditions. Articulation of the teeth in the upper and lower arches can also be determined by the disclosed method and apparatus.

In its preferred form, one or more sensors could emit a broadband outgoing pulse, and a series of echoes would be received and recorded by multiple sensors. These received signals would be reconstructed into a three-dimensional image, taking into account the possible mode conversions, i.e., a received subsurface echo could be considered a longitudinal, shear or surface wave response, each of which implies a different location for the reflecting target.

In its more rudimentary form, the disclosed method provides a way to collect diagnostic data in the absence of three dimensional volume data. By simply inserting broadband sound energy into the dental structure, the resonance of the structure can be measured. This approach is well known in industrial inspection as a "tap test" or "quarter test." By comparing the current resonance of the structure to a prior reading on the same structure, changes in condition can be detected. Similarly, comparing the current resonance of a tooth to a database of typical resonances for similar dental structures can provide the dentist with significant diagnostic insight. For example a whole, intact tooth will resonate at a sound frequency determined by the dimensions of the tooth. If the tooth becomes cracked, then one of the dimensions is reduced by half or more, which can cause the resonant frequency to double—note that an intact tooth will exhibit similar resonances regardless of the location scanned, but each segment of a cracked tooth will exhibit unique resonances. Likewise, partial damage, such as a small crack or carious lesion, can cause sound propagation properties to change enough to enable detection of a small shift in frequency. Finally, resonances also are influenced by the coupling of the tooth to surrounding structures, such as adjacent teeth and the jaw, which adds another dimension to the diagnostic capability of the scanning method.

Extrapolating the resonance test further, each tooth can be interrogated using a localized resonance measurement. By focusing a broadband sound beam at a specific location of a tooth, the thickness of the enamel and dentin at that location will cause a resonant response from which the thickness can be estimated. The focused sound beam can be scanned over the available surface of each tooth (including surface below the gum line) to map the thickness/resonant response over that full area. These data can be compared to previous measurements to detect a change in condition indicative of a variety of dental issues, including carries or cracks.

Because an ultrasonic dental exam can be retained for future reference, subsequent exams can be compared to previous exams, and changes in condition can be detected. This allows for the application of RADAR imaging techniques to be applied to improve detection of changed features. RADAR technology routinely relies on image averaging and image subtraction techniques to detect the smallest features. Currently, ultrasonic inspections in industry or medical applications cannot use these techniques because the component or patient is only inspected once in a given configuration, and changes in configuration do not allow valid indications.

A general understanding and appreciation of the disclosed method and apparatus is facilitated by referring initially to FIG. 1, a block or schematic diagram depicting the instrumentation employed in a preferred embodiment. Included in the instrumentation, of course, is the sensor or transducer array providing a plurality of transducers which will both emit and receive ultrasonic wave activity. On electrical excitation, the transducer emits an outgoing ultrasonic pulse which, in this instance, if aimed correctly, travels through a couplant and impinges on the surface of the dental structure (s) to be mapped or studied. The outgoing or emitted pulse, after contacting the surface of the dental structure being studied, is partially transmitted into the dental structure. Any physical boundary within the dental structure comprising a change in density or modulus will create an echo pulse, which will be detected by the transducer array. This reflected echo pulse signal will then be amplified by an amplification means and sent to an analog/digital converter which is part of the computing means for comparison with the emitting pulse. By converting the reflected pulse signal to a digital code and then comparing it with the code of the emitted signal, software in the computing means can recreate and display a two or three dimensional depiction of the structure being studied. Note that this data will be most coherent for the sound energy entering and leaving the tooth through the smooth surfaces on the side of each tooth.

Figure 2:
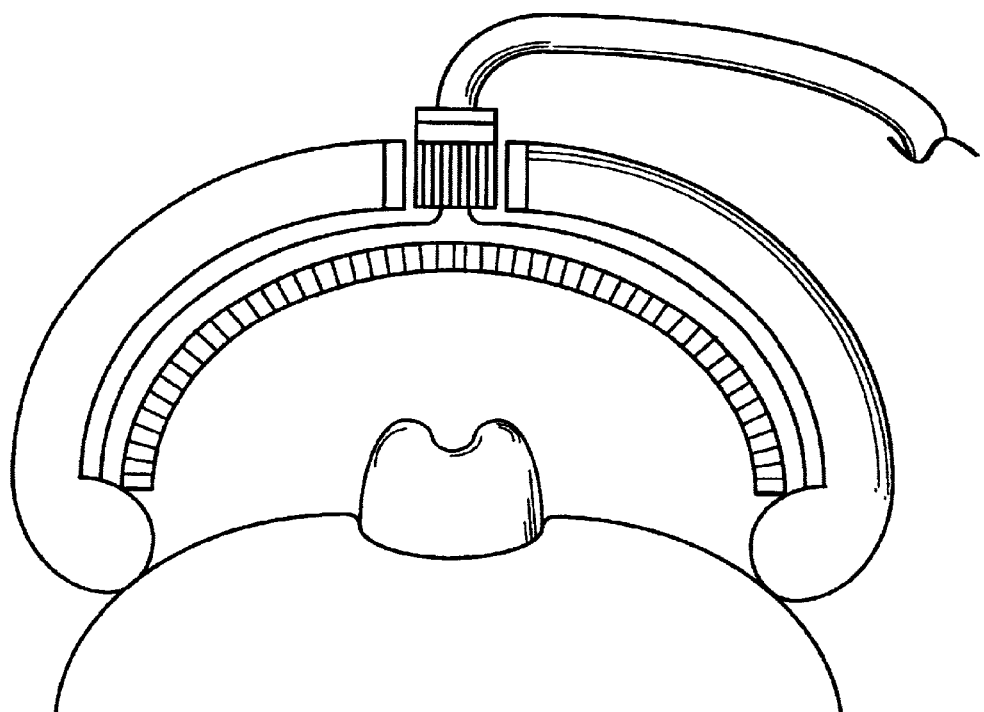
FIG. 2 is an axial cross-section view of the sensor array of an ultrasonic mapping apparatus within its housing.
Figure 4:
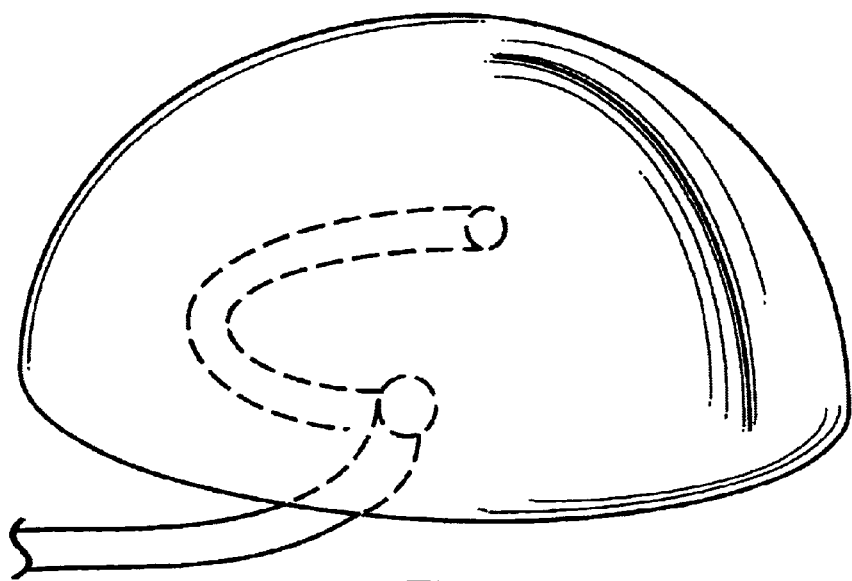
FIG. 4 is a transparent schematic showing the housing of an ultrasound mapping apparatus with a pivoting articulating means for the sensor array.

For further understanding of the method disclosed herein, please refer to FIG. 2. Bear in mind that the oral structure to be studied will typically be a relatively inaccessible tooth. In the actual practice of the invention, an arc-shaped, linear array of ultrasonic sensors is rotated around and over the tooth. Referring to FIGS. 2 and 4, it will be apparent that in a preferred embodiment the sensor array, which is typically a plurality of transducers, is positioned on a rotating arc within a shell, which acts as the housing for the array. The housing and swinging arc can be structurally compared to an ice cream scoop with a lever activated arc for separating the ice cream from the bowl of the scoop. The bowl of the scoop is comparable to the housing of the apparatus and the lever activated arc is comparable to the sensor or transducer array.

Between the transducers and the tooth is a volume of space filled with a couplant, a material which allows sound to be conducted from the transducer into the tooth. Although air-coupled transducers are available, the presence of blood and gum tissue around the tooth makes that approach extremely difficult. Instead, the preferred embodiment uses water as the couplant, with blood and even gum tissue having sound transmission properties similar enough to water, that either one may be present without significant degradation of the sound energy.

The primary function of the housing is to contain and guide motion of the transducer array; and, in a preferred embodiment, the housing will be designed to be situated over all of the exposed tooth to be studied; and, where necessary, the housing will also serve to confine a liquid couplant.

In order to fit snugly over the tooth to be mapped, the open rim of the housing will be fitted with a gasket of soft, deformable material. It will be developed to fit on the gum and around the tooth. It is desirable for the gasket to be relatively water tight to contain the couplant. When the housing is securely in place, a drive mechanism situated in the housing and in electrical communication with the sensor array, can be activated to swing the sensor array in an arc, usually about 150° C., over and around the tooth. While articulating in this fashion, the transducers on the articulating arc can be electronically activated to vibrate and emit ultrasonic pulses, some of which will penetrate the tooth and be returned to other transducers on the arcing sensor array. These echo or reflected pulse signals, after being detected by transducers on the array, can be collected, analyzed and compared to produce a recreation of the tooth or dental structure being examined.

To recap, somewhat, when electrically activated, the transducer will vibrate and create sound waves which will travel from the sensor array through the liquid couplant to the surface of the prepared tooth, and finally to the interior of the tooth. The sound waves are reflected by internal structural variations, creating echo pulses, back to the array of transducers and "detected". The sensor will "detect" the echo signal. The echo signal is converted to an electrical signal, which is amplified, digitized and downloaded to a computer containing software capable of analyzing the digitized signal. By collecting reflected or scattered signals from as many angles as possible, the computer will have sufficient time-of-flight measurements to perform a tomographic computation to model or map the tooth volume.

As indicated previously, a prototypical sensor array has been designed and will be constructed to resemble an ice cream scoop with a swinging arc. It has 150° C. with 128 sensor elements in a 1 cm diameter. Each element is 0.1 mm when situated radially and 2 mm when situated axially. The sensor elements have been designed to a broadband sound pulse with a center frequency in the range of 10–20 MHz, with a sound absorbing material bonded on the back side. Based on the prototype it is to be observed that the size, shape and arrangement of the sensor elements could vary considerably from those currently employed. Furthermore, altering the combination of wavelength and axial focus can affect and fine-tune the resolution desired.

The shell with the semicircular array of sensor elements arranged on the arc within the "scoop" is placed over the tooth. Because of the innovative arrangement of the sensors, teeth in both the upper and lower jaws are equally accessible to scanning. The arc of transducer sensor elements is then rotated over and around the tooth as it rotates 150° C. within the hemispherical shell acquiring a set of signals from the scattered waves at preselected intervals. The intervals are selected to achieve the desired image resolution and can be as numerous as necessary within practical limits. The ultrasonic pulses emanating from the emitter are generated in response to a positional indicator encoded within the shell; and they can be controlled from a rheostat on the drive mechanism, from a timing circuit for an array moving at a predetermined speed, or from a telemetry unit within the sensor array.

The drive mechanism is contained within the shell to minimize patient discomfort and is typically a spring-loaded cable, or could just as easily be electronic. And furthermore, an hydraulic drive mechanism has certain advantages: The drive fluid could conveniently be water at low pressure and could also be the same liquid as the couplant.

The couplant occupies the space between the shell and the prepared tooth. The couplant is ideally contained within the shell by a circumferential seal; or alternatively, containment is ignored and disregarded by providing a constant, laminar flow into the shell and thus continuously surrounding the prepared tooth.

Figure 3:
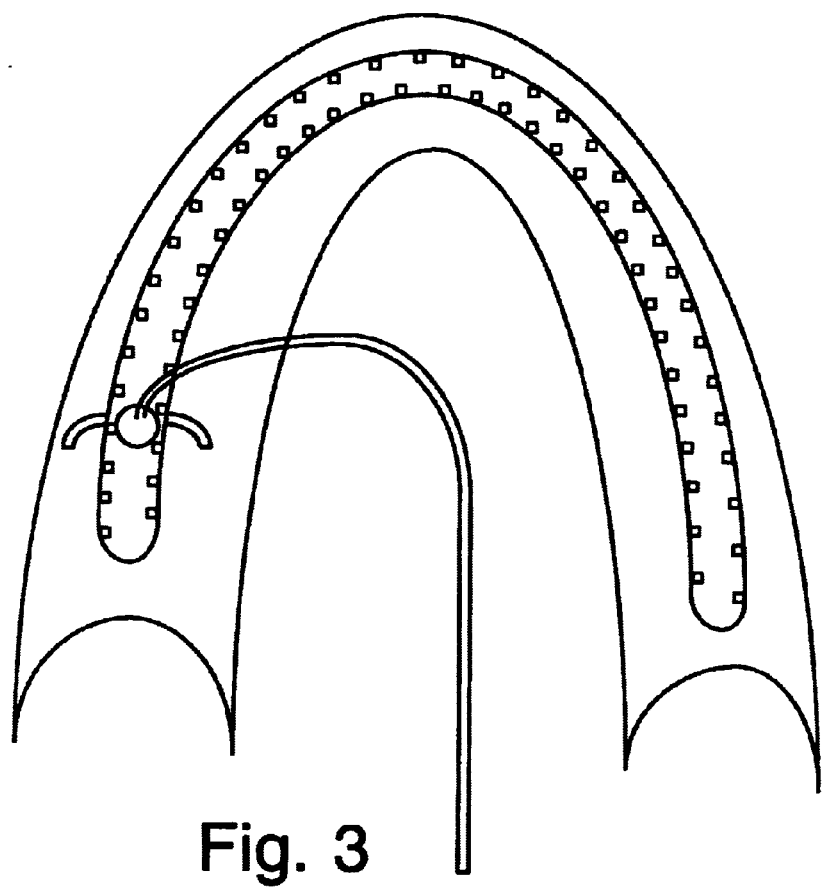
FIG. 3 is a partially transparent schematic for an ultrasound mapping apparatus for all structures in a jaw.

Other embodiments of the housing and sensor array can be arranged to perform other mapping tasks within the oral cavity. For instance, FIG. 3 depicts a partially transparent schematic representation of a housing and sensor array combination that would be suitable for mapping all structures within either an upper or lower jaw. In this embodiment, instead of arcing over and around each tooth, the sensor array can be driven over and around all the teeth in the jaw. This is accomplished by having an arched housing in a U-shape containing a transducer array formed into a 180° C. arc attached to a drive mechanism capable of moving the array over and around all teeth in the jaw. Any of a variety of drive mechanisms could be used including teeth 11 and gear or drive screws.

In FIG. 4, an alternative embodiment of the transducer array is depicted. Here the housing and transducer array are similar to the design arrangement found in FIG. 2, but in this instance the transducer array is driven by a pivoting drive mechanism. Such an arrangement will enable the transducer array to move with greater maneuverability, thus permitting more resolutions and a finer re-creation of the oral structure.

The transducer array is typically located in a position proximal to where the data are to be acquired, and a trigger pulse initiates the sequence of data collection. Although the transducer elements (sensors) could be activated simultaneously, or in a phased sequence crosstalk between elements is eliminated by triggering the sensors one at a time. The element then waits for a return echo, which is converted into a measurable signal. And although only one sensor is triggered at a time, all sensors are monitored simultaneously to maximize the amount of information recorded over and around the reflecting surface of the tooth. It is beneficial to monitor echo signals with all sensors because the irregular geometric features of the tooth will scatter sound in all directions.

The echoes received are transmitted through a cable to an electronic receiver positioned near the patient. The echoes are analyzed individually or as a tomographic reconstruction of the time-of-flight data to procure a two-or three-dimensional view of the tooth. The two-dimensional depictions are known as sagital slices. They can be combined with other sagital slices to form a three-dimensional phased tomographic reconstruction and a three-dimensional view of the dental structure being examined.

The acquired data can be stored as either as the reconstructed signal or as raw data. In either form, the data can be transmitted electronically to remote sites for further evaluation or archival.

By providing a means to retain data in digital form, the disclosed method can provide a training tool for new dentists. It can also create a scenario in which an inexperienced dentist can provide a diagnosis based on a vast reserve of historical data, or even obtain a second opinion without having to recommend an additional office visit.

By applying the disclosed scanning device to whole body anatomical structures, such as a human finger or knee, a three dimensional map can be generated showing the relationship between soft tissue and bone. This could be particularly valuable in determining the extent of a finger bone fracture, mapping local levels of osteoporosis, or in mapping bones, tendons, ligaments and cartilage while evaluating conditions such as carpal tunnel syndrome, tennis elbow, or corns or bunions in the foot, just to name a few.

While the foregoing is a detailed and complete description of the preferred embodiments of the disclosed method and apparatus for three-dimensional mapping of dental structures, it should be apparent that numerous variations and modifications can be made and employed to implement the all important purpose of the method and apparatus without departing from their spirit, which is fairly defined by the appended claims.

We claim:

1. A method of mapping internal structure of dental formations by emitting an ultrasonic pulse to impinge on said structure and recording an ultrasonic response of said impinged formation, said method comprising:

providing a transducer means positioned to produce an outgoing ultrasonic pulse for impinging directly on said dental formations;

measuring the ultrasonic response from said dental formation; and displaying in a representation of said response to depict the internal structure of said dental formation.

2. The method according to claim 1 wherein the outgoing ultrasonic pulse from said transducer means is a broadband excitation pulse.

3. The method according to claim 1 wherein the outgoing ultrasonic pulse from said transducer means is a swept frequency burst.

4. The method according to claim 1 wherein the displayed response is generated as a volumetric series of gated amplitude C-scans.

5. The method according to claim 1 wherein the displayed response is generated as a volumetric series of B-scans.

6. The method according to claim 1 wherein the displayed response is generated as a volumetric series of sector scans.

7. The method according to claim 1 wherein the displayed response is generated as a plot of a resonant frequency response of the dental formation.

8. The method according to claim 1 wherein the dental formation is a tooth.

9. An apparatus for mapping internal structure of a dental formation by emitting an ultrasonic pulse impinging on said formation and detecting an ultrasonic response from said apparatus comprising:

a transducer array for emitting and detecting ultrasonic pulses;

an articulating means to move said transducer array over and around said dental formation;

a power source for activating movement of said articulating means;

an electrical power source for exciting said transducer array;

an amplification means for enhancing said ultrasonic response; and a computing for converting said ultrasonic response into an interpretable display.

* * * * *